US010746720B2

(12) United States Patent
Jennings

(10) Patent No.: US 10,746,720 B2
(45) Date of Patent: Aug. 18, 2020

(54) SOIL MOISTURE MONITORING SYSTEMS AND METHODS FOR MEASURING MUTUAL INDUCTANCE OF AREA OF INFLUENCE USING RADIO FREQUENCY STIMULUS

(71) Applicant: FarmX Inc., Redwood City, CA (US)

(72) Inventor: William E. Jennings, San Jose, CA (US)

(73) Assignee: FarmX Inc., Mountain View, CA (US)

( * ) Notice: Subject to any disclaimer, the term of this patent is extended or adjusted under 35 U.S.C. 154(b) by 242 days.

(21) Appl. No.: 15/867,594

(22) Filed: Jan. 10, 2018

(65) Prior Publication Data

US 2018/0202988 A1    Jul. 19, 2018

Related U.S. Application Data

(60) Provisional application No. 62/446,272, filed on Jan. 13, 2017.

(51) Int. Cl.
*G01N 27/26*    (2006.01)
*G01N 33/24*    (2006.01)
(Continued)

(52) U.S. Cl.
CPC ......... *G01N 33/246* (2013.01); *A01G 25/167* (2013.01); *G01N 27/025* (2013.01); *G01N 2033/245* (2013.01)

(58) Field of Classification Search
CPC ............... G01N 33/246; G01N 27/025; G01N 2033/245; G01N 33/00; G01N 33/24;
(Continued)

(56) References Cited

U.S. PATENT DOCUMENTS

RE31,023 E    9/1982  Hall, III
4,590,477 A    5/1986  Regnier et al.
(Continued)

FOREIGN PATENT DOCUMENTS

WO    WO2016110832 A1    7/2016
WO    WO2018085452 A1    5/2018

OTHER PUBLICATIONS

Smith, Adam Brook, "Soil Moisture Monitoring with Ground-Based Gravity Data," Dissertation University of Melbourne, Department of Infrastructure Engineers, 2013, 397 pages.
(Continued)

*Primary Examiner* — Melissa J Koval
*Assistant Examiner* — Courtney G McDonnough
(74) *Attorney, Agent, or Firm* — Carr & Ferrell LLP

(57) ABSTRACT

Soil moisture monitoring systems and methods for measuring mutual inductance of area of influence using radio frequency stimulus are disclosed herein. An example method includes receiving a first inductance frequency sample from a first oscillator circuit, the first oscillator circuit being coupled with one or more reference inductors; receiving a second inductance frequency sample from a second oscillator circuit, the second oscillator circuit being coupled with one or more mutual inductors that sense soil moisture inductance in an area of soil; receiving a temperature reading from a thermometer, the temperature reading being obtained when the first inductance frequency sample and the second inductance frequency sample were obtained. The example method further includes transmitting the first inductance frequency sample, the second inductance frequency sample, and the temperature reading to a receiver.

19 Claims, 15 Drawing Sheets

(51) Int. Cl.
*A01G 25/16* (2006.01)
*G01N 27/02* (2006.01)

(58) Field of Classification Search
CPC ...... G01N 27/00; A01G 25/167; A01G 25/00; A01G 25/16
USPC .... 324/654, 600, 649, 656, 76.11, 135, 139, 324/436
See application file for complete search history.

(56) References Cited

U.S. PATENT DOCUMENTS

| | | | |
|---|---|---|---|
| 5,418,466 | A | 5/1995 | Watson et al. |
| 5,445,178 | A | 8/1995 | Feuer |
| 6,014,029 | A | 1/2000 | Soto et al. |
| 6,720,908 | B1 | 4/2004 | Puglia |
| 6,891,444 | B2 | 5/2005 | Jacobsson et al. |
| 6,977,351 | B1 | 12/2005 | Woytowitz |
| 7,836,910 | B2 | 11/2010 | Dresselhaus et al. |
| 8,682,494 | B1 | 3/2014 | Magro et al. |
| 10,509,378 | B2 | 12/2019 | Jennings et al. |
| 10,533,956 | B2 | 1/2020 | Jennings |
| 2002/0170229 | A1 | 11/2002 | Ton et al. |
| 2004/0145379 | A1* | 7/2004 | Buss ............. G01N 27/223 324/664 |
| 2006/0057997 | A1 | 3/2006 | Hausdorf et al. |
| 2006/0144437 | A1 | 7/2006 | Dresselhaus et al. |
| 2009/0326723 | A1 | 12/2009 | Moore et al. |
| 2010/0257633 | A1 | 10/2010 | Pogson et al. |
| 2012/0084115 | A1 | 4/2012 | Cline et al. |
| 2013/0341420 | A1 | 12/2013 | Lister et al. |
| 2014/0088770 | A1 | 3/2014 | Masters et al. |
| 2014/0117468 | A1* | 5/2014 | Parris ............ G01N 27/221 257/414 |
| 2014/0326801 | A1 | 11/2014 | Upadhyaya et al. |
| 2015/0081058 | A1 | 3/2015 | Oliver et al. |
| 2015/0247787 | A1 | 9/2015 | Yeomans |
| 2015/0268218 | A1 | 9/2015 | Troxler |
| 2015/0278719 | A1 | 10/2015 | Schueller et al. |
| 2015/0301536 | A1 | 10/2015 | Martinez |
| 2016/0037709 | A1 | 2/2016 | Sauder et al. |
| 2016/0135389 | A1 | 5/2016 | Ersavas et al. |
| 2016/0183484 | A1* | 6/2016 | Richings, Sr. ....... G01N 33/246 239/11 |
| 2016/0202227 | A1 | 7/2016 | Mathur et al. |
| 2017/0172077 | A1 | 6/2017 | Wouhaybi et al. |
| 2017/0311559 | A1 | 11/2017 | Ebert et al. |
| 2018/0080861 | A1 | 3/2018 | Lafian |
| 2018/0129175 | A1 | 5/2018 | Jennings et al. |
| 2018/0146631 | A1 | 5/2018 | Haran et al. |
| 2018/0146632 | A1 | 5/2018 | Meron |
| 2018/0164230 | A1 | 6/2018 | Jennings |
| 2018/0164762 | A1 | 6/2018 | Mewes et al. |
| 2018/0252694 | A1 | 9/2018 | Mase et al. |
| 2018/0259496 | A1 | 9/2018 | McPeek |
| 2020/0026250 | A1 | 1/2020 | Jennings et al. |
| 2020/0068784 | A1 | 3/2020 | Oaklander et al. |

OTHER PUBLICATIONS

EnviroSCAN Probe, [retrieved on Dec. 14, 2016], Retrieved from the Internet: <URL:http://www.sentek.com.au/products/enviro-scan-probe.asp>, 3 pages.

Liquid Sensing at Radio Frequencies, Complex impedance measurement of liquid samples as a function of frequency, [retrieved on Jan. 13, 2017] Microwave Journal, Thomas J. Warnagiris, Sep. 1, 2000, (http://www.microwavejournal.com/articles/3038-liquid-sensing-at-radio-frequencies), 9 pages.

"International Search Report" and "Written Opinion of the International Searching Authority", Patent Cooperation Treaty Application No. PCT/US2017/059597, dated Jan. 25, 2018, 9 pages.

Berni et al., "Mapping Canopy Conductance and CWSI in Olive Orchards Using High Resolution Thermal Remote Sensing Imagery", in: Remote Sensing Environment 113 [online], Jun. 28, 2009 [retrieved on Jan. 4, 2018], Retrieved from the Internet: <URL:https://www.sciencedirect.com/science/article/pii/S0034425709002090>, pp. 2380-2388.

\* cited by examiner

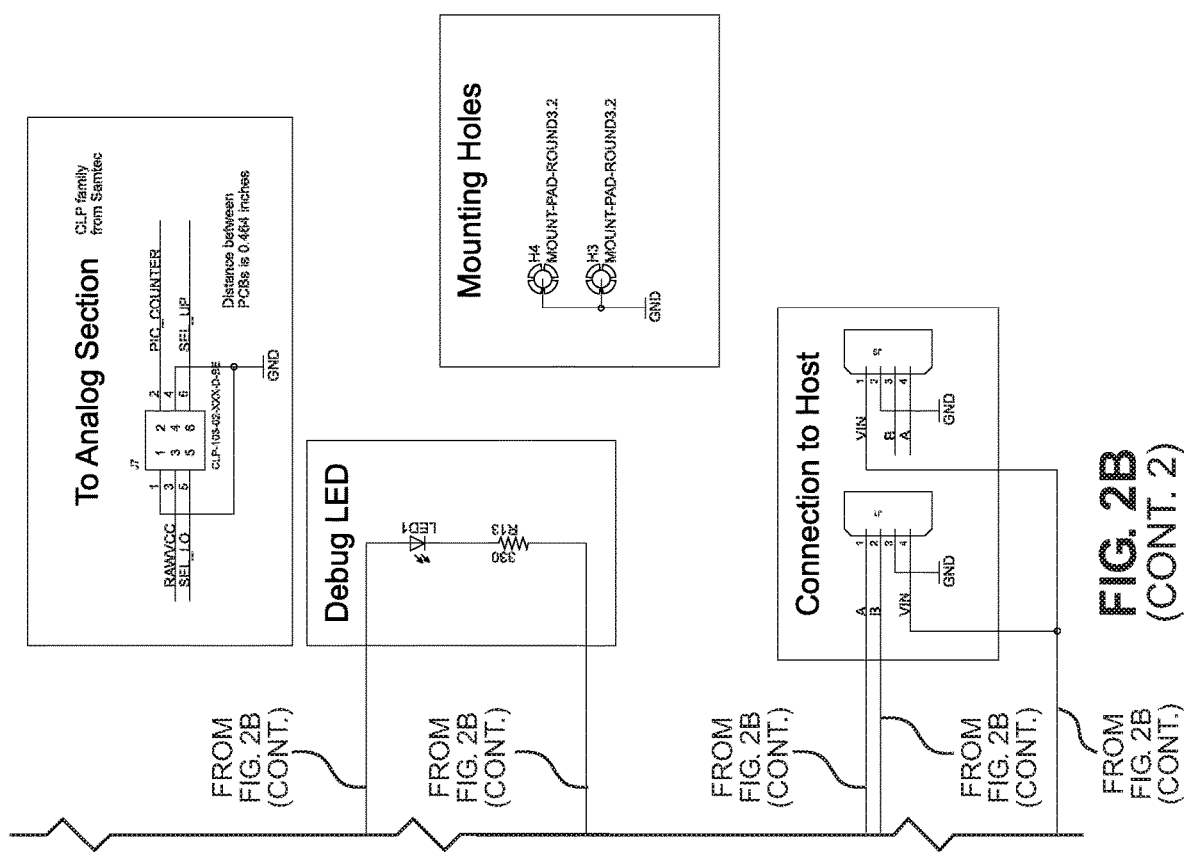

(cont. 2)

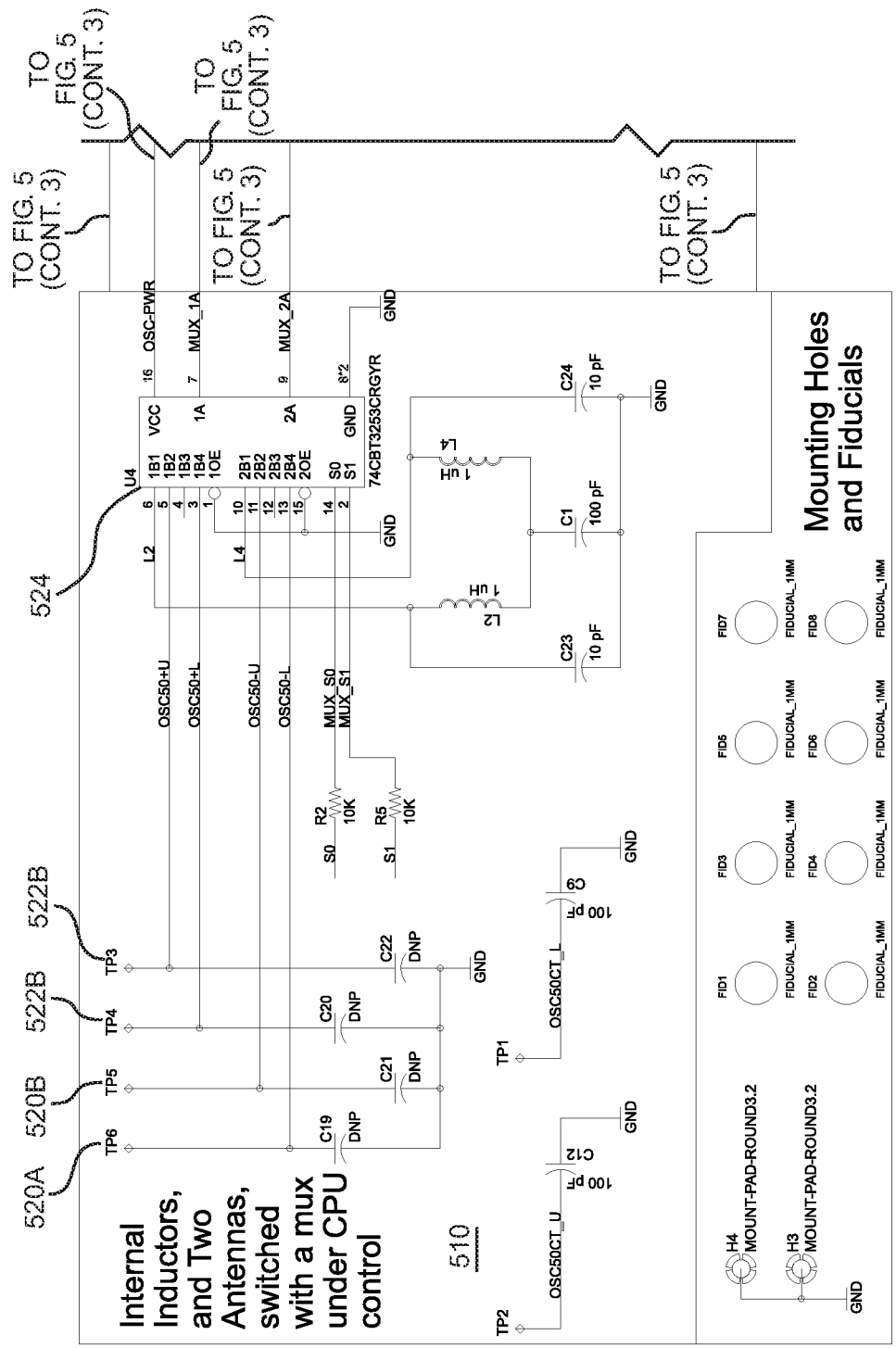
FIG. 5 (cont.2)

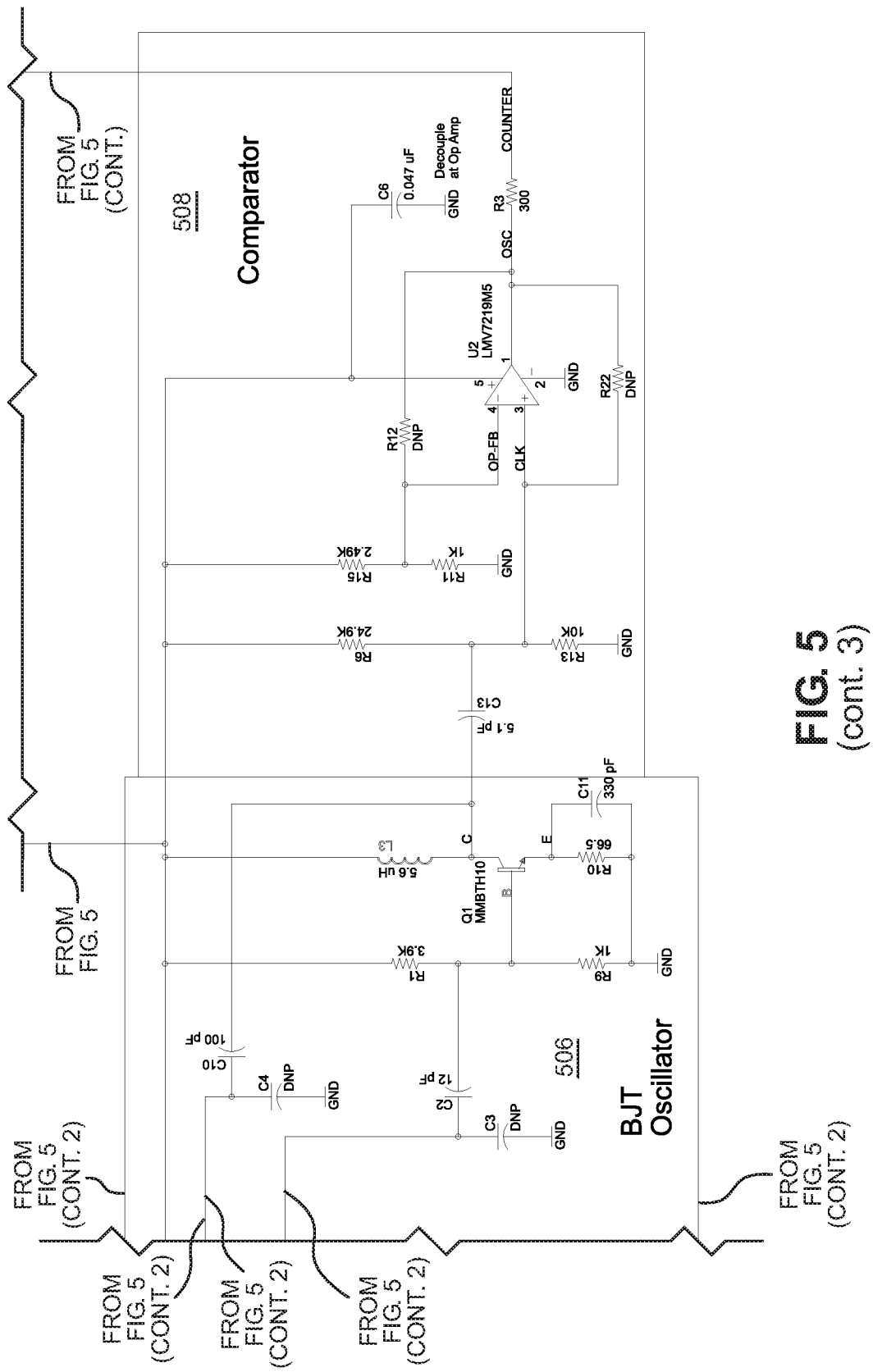
FIG. 5 (cont. 3)

SOIL MOISTURE MONITORING SYSTEMS AND METHODS FOR MEASURING MUTUAL INDUCTANCE OF AREA OF INFLUENCE USING RADIO FREQUENCY STIMULUS

CROSS REFERENCE TO RELATED APPLICATION

This patent application claims the benefit and priority of U.S. Provisional Application Ser. No. 62/446,272, filed on Jan. 13, 2017, entitled "Soil Moisture Monitoring System Apparatus Measuring the Mutual Inductance of Area of Influence Using Radio Frequency Stimulus." The aforementioned disclosure is hereby incorporated by reference herein in its entirety including all references cited therein.

FIELD OF THE TECHNOLOGY

Embodiments of the disclosure relate to soil moisture monitoring. Some non-limiting embodiments comprise one or more moisture sensor circuits that each utilizes mutual inductance to determine soil moisture content in a given area of soil.

SUMMARY

Various embodiments of the present disclosure relate to a soil moisture monitor device. In some embodiments the soil moisture monitor device includes: a first oscillator circuit coupled with one or more reference inductors to emit a first inductance frequency; a second oscillator circuit coupled with one or more mutual inductors to emit a first inductance frequency into an area of soil; a microcontroller electrically coupled to the first oscillator circuit and the second oscillator circuit; and a housing positioned within the area of soil, the housing comprising an inner tubular substrate that receives the one or more reference inductors, the one or more mutual inductors, the first oscillator circuit, the second oscillator circuit, and the microcontroller. In some embodiments, the microcontroller is configured to: obtain a first inductance frequency sample using the one or more reference inductors; obtain a second inductance frequency sample using the one or more mutual inductor; obtain a temperature reading from a thermometer; and transmit the first inductance frequency sample, the second inductance frequency sample, and the temperature reading to a receiver.

Various embodiments of the present disclosure relate to a soil moisture monitor method. In some embodiments the soil moisture monitor method includes: receiving a first inductance frequency sample from a first oscillator circuit, the first oscillator circuit being coupled with one or more reference inductors that sense a reference inductance; receiving a second inductance frequency sample from a second oscillator circuit, the second oscillator circuit being coupled with one or more mutual inductors that sense soil moisture inductance in an area of soil. In some embodiments the soil moisture monitor method includes receiving a temperature reading from a thermometer, the temperature reading being obtained when the first inductance frequency sample and the second inductance frequency sample were obtained; and transmitting the first inductance frequency sample, the second inductance frequency sample, and the temperature reading to a receiver.

Various embodiments of the present disclosure relate to a soil moisture monitoring system comprising: a power supply; a time division multiplexer communicatively coupled via a bus to the power supply; a microcontroller communicatively coupled to the time division multiplexer, the microcontroller housed within a housing such as a PVC pipe; an upper oscillator communicatively coupled to the microcontroller, the upper oscillator within the PVC pipe; an upper internal inductor communicatively coupled to the upper oscillator, the upper internal inductor within the PVC pipe; an upper external inductor further comprising an antenna communicatively coupled to the upper oscillator, the upper external inductor and the antenna within the PVC pipe; a lower oscillator communicatively coupled to the microcontroller, the lower oscillator within the PVC pipe; a lower internal inductor communicatively coupled to the lower oscillator, the lower internal inductor within the PVC pipe; a lower external inductor further comprising an antenna communicatively coupled to the lower oscillator, the lower external inductor and the antenna within the PVC pipe; and a thermometer communicatively coupled to the microcontroller, the thermometer within the PVC pipe.

Various embodiments of the present disclosure relate to a soil moisture monitoring method. In some embodiments the soil moisture monitoring method includes: transmitting power to a time division multiplexer; transmitting power from the time division multiplexer to a microcontroller; transmitting identifying information from the microcontroller via a bus to the time division multiplexer; transmitting power from the microcontroller to an oscillator; transmitting power from the oscillator to an internal inductor, the internal inductor not in proximity to soil or soil moisture; transmitting a frequency by the oscillator for a predefined time period as provided by the microcontroller; counting by the internal inductor for the predefined time period a number of reference pulses; turning off the power to the oscillator after the predefined time period; switching a circuit from the internal inductor to an external inductor and antenna in proximity to soil or soil moisture; determining a current soil temperature by a thermometer; turning on the power to the oscillator; waiting for the oscillator to settle; transmitting a frequency by the oscillator for a predefined time period as provided by the microcontroller; counting by the external inductor for the predefined time period a number of soil moisture pulses (inductance of soil); turning off the power to the oscillator; repeating the above steps for a lower second circuit; transmitting for both circuits the reference pulses, the current soil temperatures and the soil moisture pulses via a bus to an external memory; and turning off the power from the time division multiplexer to the microcontroller. Some methods include applying a temperature compensation factor to a difference of the reference pulse and the soil moisture pulse for each circuit in order to determine a volumetric water content. Some methods include temperature compensation factor that is based on the oscillator performance varying with soil temperature. In some embodiments the frequency used by the one or more oscillators is above 30 megahertz.

BRIEF DESCRIPTION OF THE DRAWINGS

While this technology is susceptible of embodiment in many different forms, there is illustrated in the drawings, and will herein be described in detail, several specific embodiments with the understanding that the present disclosure is to be considered as an exemplification of the principles of the technology and is not intended to limit the technology to the embodiments illustrated.

It will be understood that like or analogous elements and/or components, referred to herein, may be identified throughout the drawings with like reference characters. It is further understood that several of the figures are merely schematic representations of the present technology. As such, some of the components may be distorted from their actual scale for pictorial clarity.

DETAILED DESCRIPTION OF EXEMPLARY EMBODIMENTS

Figure 1:
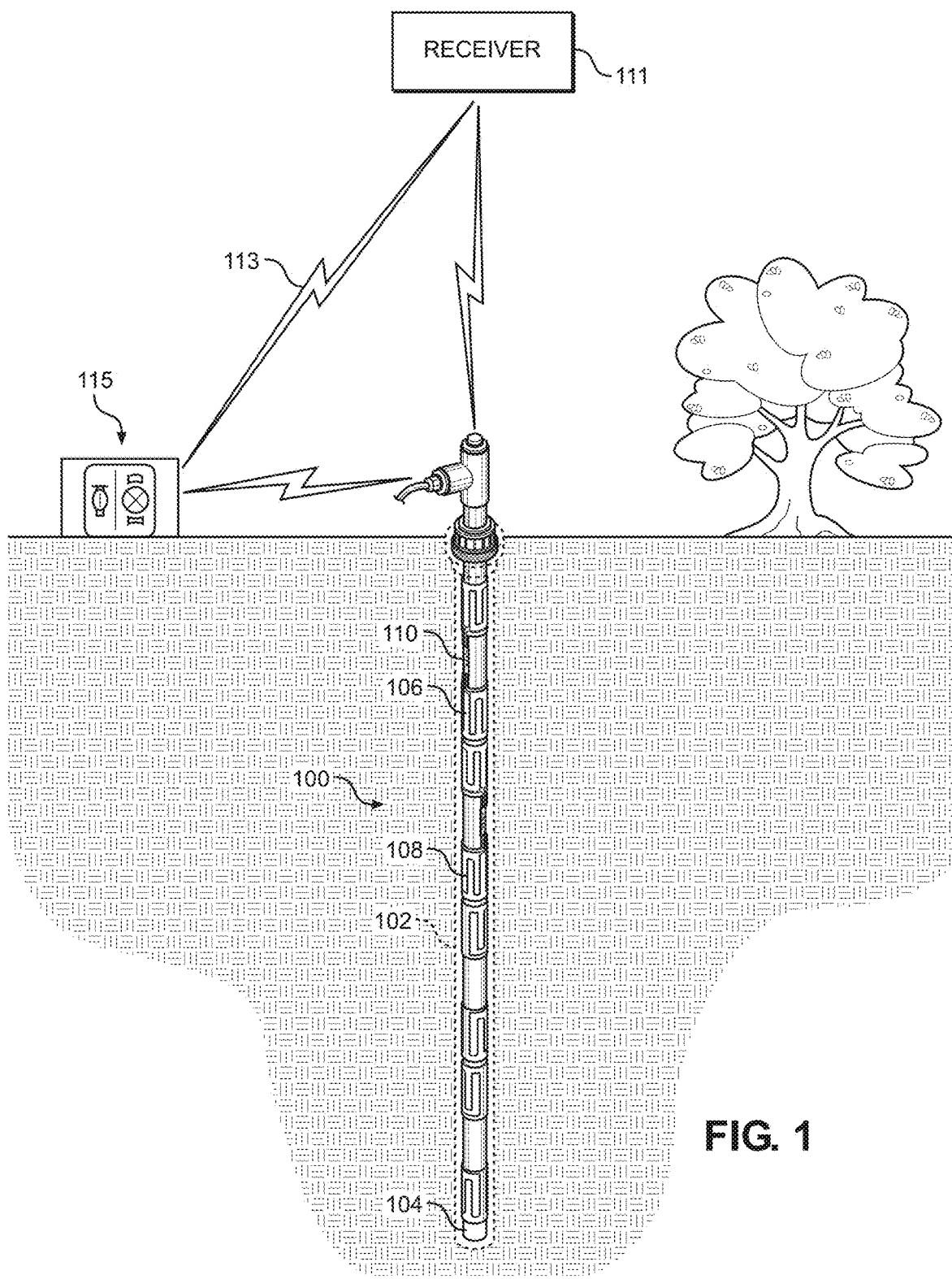
FIG. 1 is a perspective view of an example device that comprises a plurality of soil moisture sensors, constructed in accordance with the present disclosure.

The exemplary embodiments provided herein are for use in irrigation agriculture, particularly permanent crops. More specifically, the exemplary embodiments comprise a system and method for accurately measuring the volumetric water content of soil using a cost effective apparatus.

For context, of the principal ways that farmers manage their irrigation is with soil moisture sensors. In brief, plants uptake their water from the soil through their root structure. Their ability to do so is impacted by the amount of water in the soil, the soil tension, and the suction force needed by the roots to absorb water.

Other sensor designs have emulated the root of a plant, and measure the water tension in the soil. These are known as tensiometers. There are sensors that look like forks that have two parallel probes about an inch apart and measure the capacitance between the probes. This is calibrated to the amount of moisture, and the calibration is dependent on the soil type that the probe measures. There are probes that use gymsum blocks that absorb water, and as these sensors absorb water their resistance reduces changes in a manner that is correlated to the amount of water absorbed. These probes have a short lifespan, as the process of absorbing moisture causes them to deteriorate. Further, their installation takes weeks before readings are meaningful.

Liquid sensing using radio frequency techniques is a known mechanism in industrial settings. One such reference would be: "Liquid Sensing at Radio Frequencies, Complex impedance measurement of liquid samples as a function of frequency," Microwave Journal, Thomas J. Warnagiris, Sep. 1, 2000.

Until now, complete soil moisture sensors have not been produced in a manner that are effective for agriculture, using radio frequency sensing, that are low power, easy to install, and can measure large volumes of soil accurately.

The systems and methods provided herein include a soil moisture sensor that is highly accurate, measures a larger volume of influence than other sensors, easy to install, and operates without soil specific calibration requirements.

Soil moisture sensors disclosed herein rely on the Van der Waals bonding properties of water, which describes the force between the permanent dipole of a water molecule and the induced dipole from a radio frequency stimulus (known as the Debye force). When a radio frequency pulse stimulates water, it will move. The more water there is, the harder it is for the same power level to cause the water to move—so there is a higher effective electrical impedance.

The exemplary systems and methods provided herein measure the inductance of the soil by mutually coupling an inductor(s) in the sensor to the soil, and including that mutual inductance as part of a tank circuit in an oscillator.

Example oscillator circuits also have a reference inductance that can be switched into the oscillator circuit as an alternative inductor. The frequency is measured for the two configurations of the oscillator (one with the inductor that is mutually coupled to the soil moisture, and the second configuration of an internal inductor). The difference of the two frequencies corresponds to the moisture content of the soil being measured.

According to various exemplary embodiments, the sensor system is hosted by a head-end that may be connected either directly to a computer for making measurements, or connected to a mesh or cellular radio controller. Either of these intelligent devices power on the sensor, and the sensor responds with measurements for both a calibration (internal) frequency, and a frequency that corresponds to the inductance of the soil being measured, and the temperature of the sensor.

In various exemplary embodiments, the soil moisture sensor is controlled by a microcontroller. When powered, the microcontroller wakes up, selects an internal inductance frequency, and powers on the oscillator(s). After waiting for a settling period for the oscillator(s) to stabilize, the frequency is read by an internal counter. Settling periods are not required for every embodiment.

Then the power for the oscillator circuit is turned off, the sensor mutual inductor is selected, and the power for the oscillator is re-enabled. Also, power cycling of oscillators is not required in every embodiment.

After a settling period, the frequency is again sampled by the microcontroller. Then the oscillator is powered-off. The temperature is read with a digital thermometer. These results are then sent by the microcontroller over a serial link to the host computer (e.g., receiver). One example of such a communications link can be a shared RS-232 interface.

If there are multiple sensors installed into a larger system, each of the controllers wake up at different times, identified by a controller ID programmed in the non-volatile memory, and share the same power, ground, and serial communication signals. The communication signals are enabled by each microcontroller in a time-division manner based on device ID.

The host controller, according to various exemplary embodiments, can either apply the needed algorithms to convert the sensor counter values, and the temperature to the volumetric water content, or it may select to transmit this information this to a server for later processing in a similar manner.

The sensor requires knowing the difference in frequency between the two inductors sampled, and also the temperature of the sensor when the measurements were taken. By calibrating the values of the frequencies in both air, and fully saturated water for each sensor—one can calculate the moisture content by linearly interpolating the frequency change based on moisture content. As the oscillator is known to change its frequencies due to temperature, a further adjustment is applied, commonly known as a temperature compensation.

Using the exemplary procedures described herein, the sensor has been demonstrated to accurately measure the moisture content, independent of material the moisture is suspended in, with an R-squared correlation of 0.92 or better.

The exemplary soil moisture sensor includes a hand wound center-tap sensor inductor, that couples with soil moisture, with a characteristic inductance of 1.4 uH, 18 gauge solid copper wire wound on a half inch SharkBite PEX Tubing with Oxygen Barrier, inserted into a three quarter inch diameter PVC pipe.

FIG. 1 is an example soil moisture device 100 constructed in accordance with the present disclosure. In various embodiments, the device 100 comprises an outer tubular housing 102 and an inner tubular substrate 104. In some embodiments, sensor units of the device 100 are mounted on an outer surface of the inner tubular substrate 104. The inner tubular substrate 104 can be inserted into an outer tubular housing.

In some embodiments, the sensor unit comprises a two or more antennas, such as antenna patch 106 and antenna patch 108 mounted on an outer surface of the inner tubular substrate 104. A soil moisture sensor circuit (sensor circuit 110) is positioned between and in electrical communication with the antenna patches 106 and 108 (also see FIG. 2A). In accordance with the present disclosure, several sets of sensor units, each comprising two antennas and a sensor circuit are located along the outer surface of the inner tubular substrate 104. Each of these sensor units can be addressed using a unique identifier.

It will be understood that the antenna patches 106 and 108 function as inductors, and thus, in some descriptions the terms antenna and inductor may be used interchangeably. In some embodiments, each antenna patch can comprise one or more individual antenna elements. In one or more embodiments, each antenna patch comprises at least two antenna elements.

In various embodiments, antennas can be referred to as either an upper or lower antenna (or upper/lower inductors). In general, the designation of upper or lower relates to a position of device 100 when located in the soil. For example, antenna patch 106 is an upper inductor and antenna patch 108 is a lower inductor when the device 100 is inserted into the soil. The upper inductor will be used to sense a reference inductance and the lower inductor will be used to sense a soil moisture inductance.

The device 100 can communicate with both a receiver 111 as well as an irrigation controller 115 in some embodiments. The device 100 can control operations of the irrigation controller 115 directly or indirectly through the receiver 111. In some embodiments, the receiver 111 can comprise a server in an irrigation control system. Alternatively, the receiver can include any device that is configured to receive, transmit and/or process the messages generated by a sensor circuit 110 of the device 100.

Figure 2A:
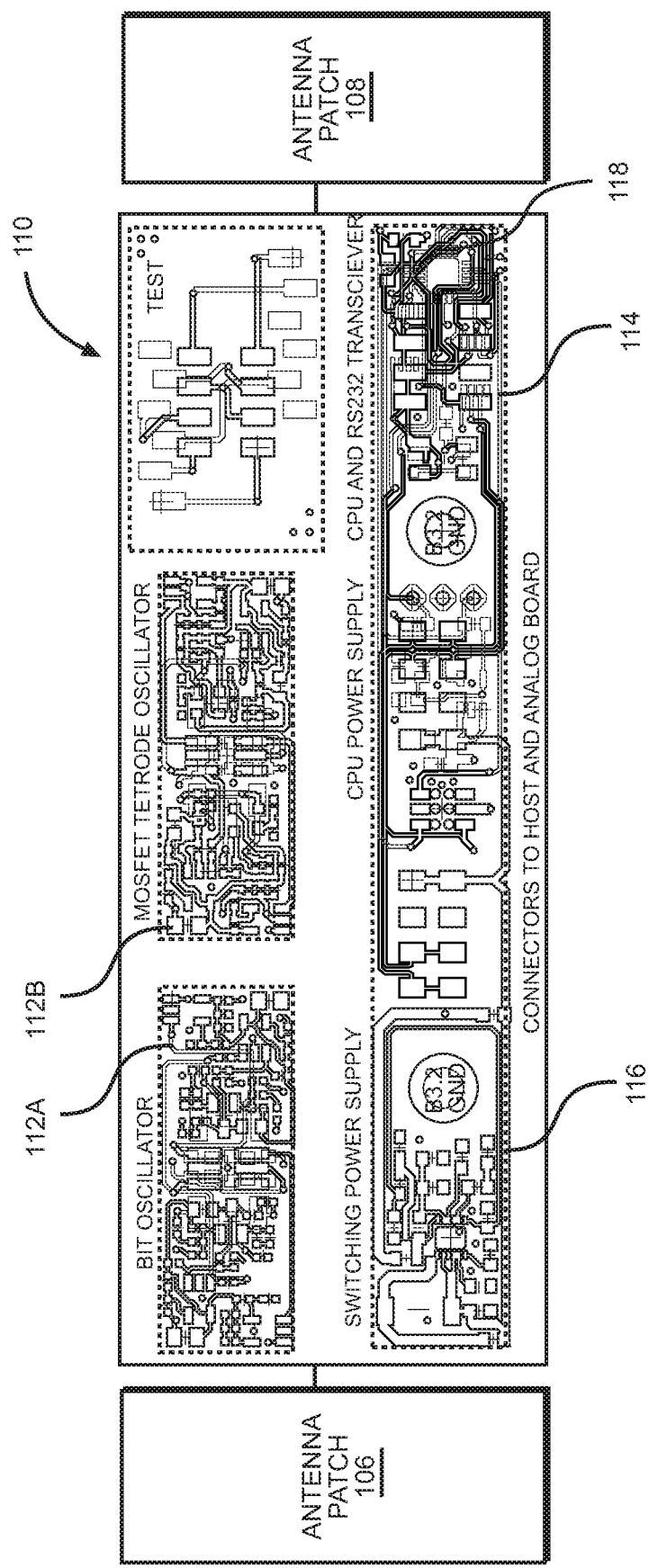
FIG. 2A is a schematic diagram of an example soil moisture sensor circuit used in a soil moisture sensor of the present disclosure.
Figure 2B:
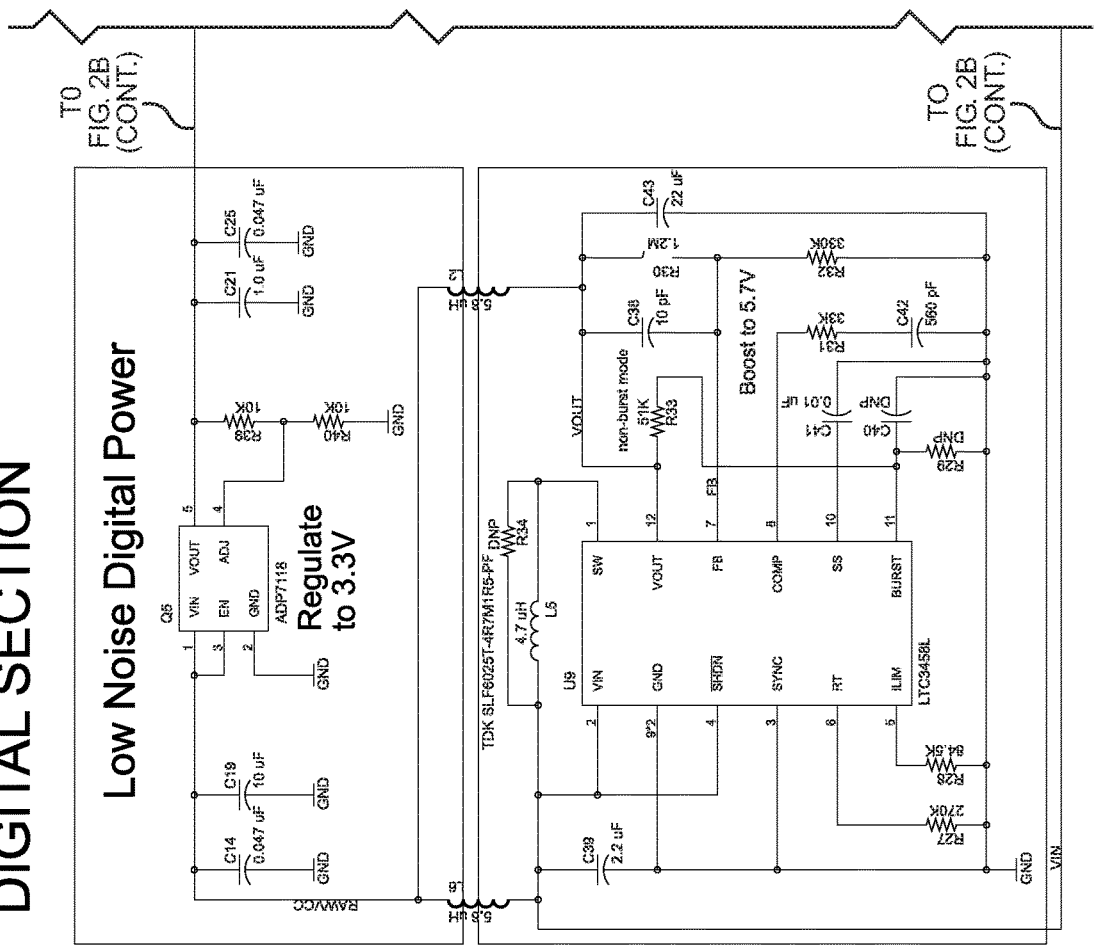
FIG. 2B is a close up of the schematic diagram of FIG. 2A.

As illustrated in FIGS. 2A and 2B, the sensor circuit 110 of FIG. 1 comprises one or more transistor circuits 112A and/or 112B, a microcontroller 114 (e.g., programmable interface circuit or PIC), a digital power supply 116, a transceiver 118, and a temperature sensor 120. In general, FIG. 2A is a macro-schematic diagram of the sensor circuit 110 and FIG. 2B is a detailed schematic diagram of the sensor circuit 110 of FIG. 2A.

Figure 2B:
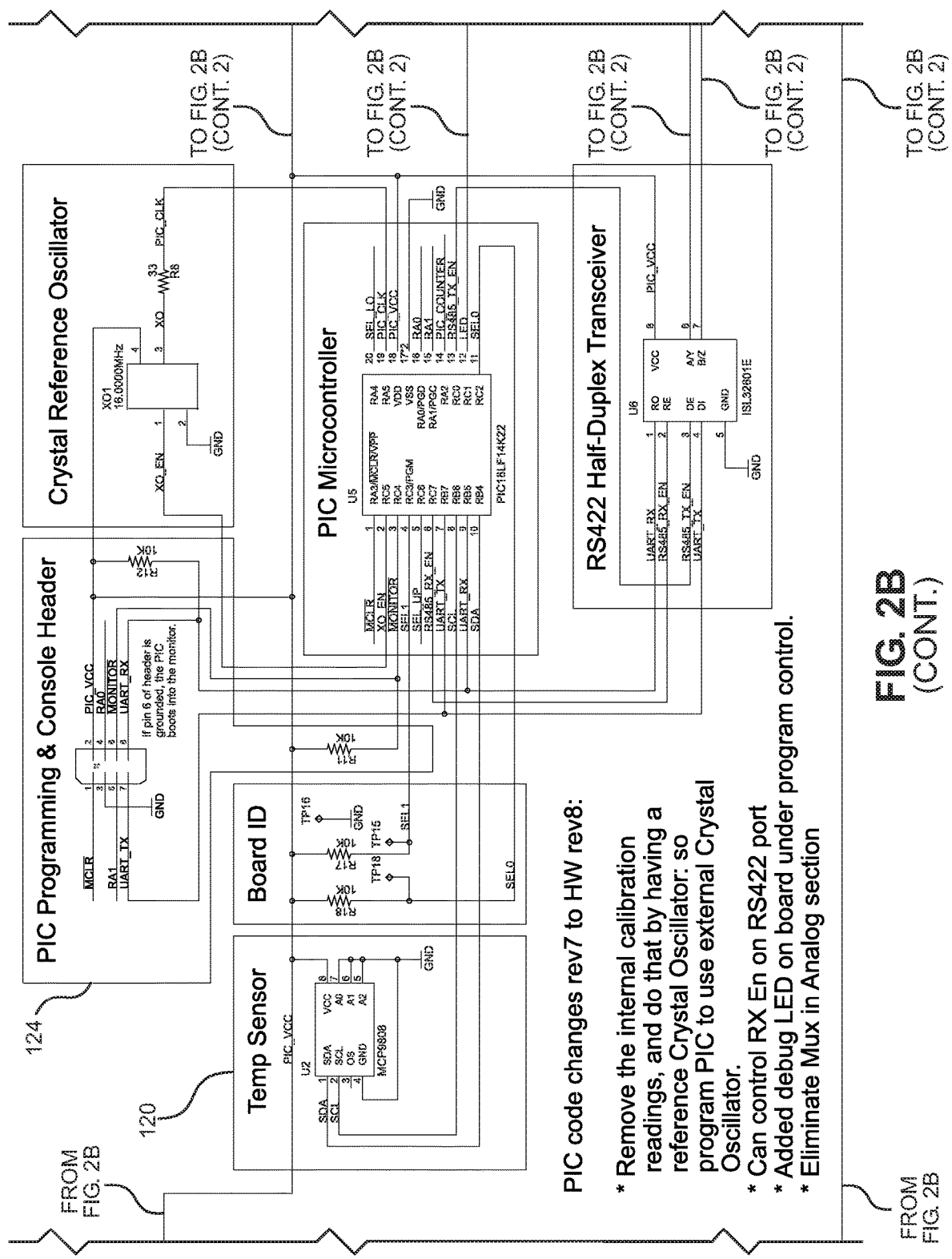

Referring to FIGS. 1-2B, the sensor circuit 110 can communicate with a receiver 111 (see FIG. 1) over a network connection 113, which can comprise a direct connection through a cellular network or indirect connection through a mesh network of other sensors. The sensor circuit 110 can also comprise a head-end that is connected either directly to a computer for making measurements, or connected to a mesh or cellular radio controller. Any of these devices such as a head-end or receiver can power on the sensor circuit 110, and the sensor circuit 110 responds with measurements for both a calibration (internal) frequency, and a frequency that corresponds to the inductance of the soil as measured, as well as a temperature of the sensor.

In various embodiments, the sensor circuit 110 can be used to selectively adjust irrigation in the area of soil that it is measuring. This can be accomplished through control of automatic pump and/or valve actuators and transducers. For example, when a soil moisture content is calculated that indicates that the area of soil has a moisture content that is below an expected moisture threshold, the sensor circuit 110 can be configured to transmit a signal that selectively adjusts pumps and/or valves of an irrigation system to increase and/or decrease the flow of water to an area of soil. An example irrigation controller 115 (e.g., a sprinkler controller) can be controlled using the sensor circuit 110 or otherwise by the receiver 111.

Thus, the microcontroller can be configured to use moisture thresholds. In other embodiments, the receiver utilizes moisture thresholds and performs moisture content comparisons to these thresholds.

Thus, the microcontroller can selectively adjust operation of an irrigation system through direct or indirect control of automatic pump and/or valve actuators and transducers.

FIG. 2B also includes a detailed view of a digital section of the sensor circuit 110. In some embodiments, a digital section of the sensor circuit 110 that comprises the microcontroller 114, the digital power supply 116, the transceiver 118, and the temperature sensor 120 can also further comprise a board ID module that provides a unique device ID that is used to identify and address messages to the sensor circuit 110 on a network. The digital section can also comprise a programming and console header 124 that provides an interface that allows external devices to interact with the microcontroller 114 for programming instructions into the microcontroller 114. The programming and console header 124 also provides an interface to a digital monitor or user interface, such as a screen or touchscreen device.

In some embodiments, the transceiver 118 comprises an RS422 protocol half-duplex transceiver, although other transceivers and protocols can also likewise be utilized in accordance with the present disclosure.

In general, the transistor circuit selected for the sensor circuit 110 can comprise either a bi-junction transistor (BJT) or a tetrode transistor, such as a MOSFET tetrode. In embodiments where a BJT is used, the BJT implements two oscillators, which each couple to one of the antenna patches 106 and 108. In embodiments where a tetrode transistor is used the tetrode transistor implements two oscillators, which each couple to one of the antenna patches 106 and 108.

Figure 3:
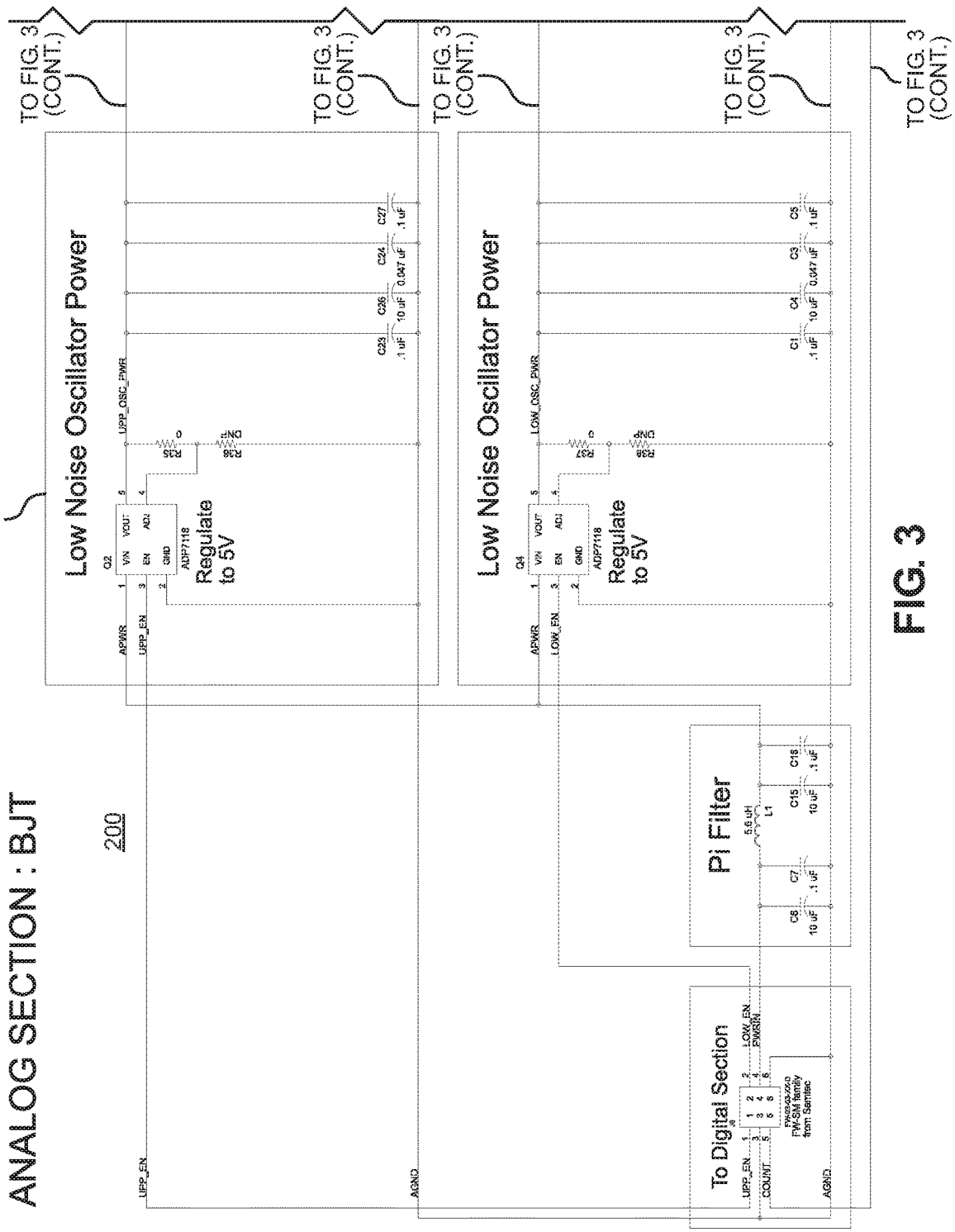
FIG. 3 is a schematic diagram of an example bi-junction transistor of a soil moisture sensor circuit of FIG. 2A.
Figure 3:
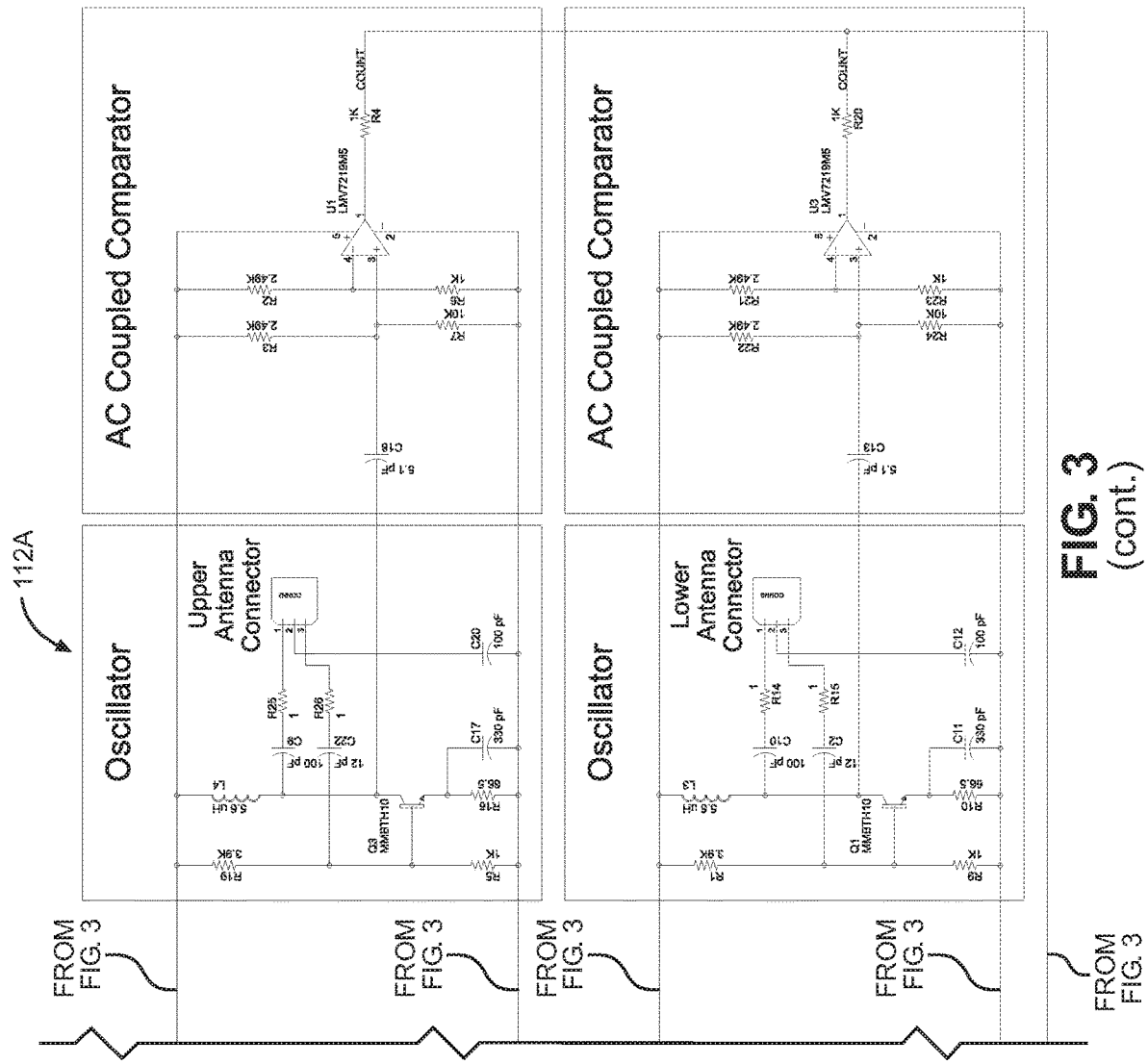

FIGS. 1-3 collectively illustrate a transistor circuit 112A in the form of a bi-junction transistor (BJT) circuit 200. The BJT 200 comprises a low noise oscillator power supply 202, a first oscillator 204 coupled with an upper antenna, such as antenna patch 106 (see FIG. 1), and a second oscillator 206, coupled with a lower antenna, such as antenna patch 108 (see FIG. 1).

A first alternating current (AC) comparator 208 counts pulses in a first inductor frequency sample, based on signals received from the first oscillator 204 using the antenna patch 106. In general, the first oscillator 204 will produce a signal with a selected frequency through the antenna patch 106.

This signal is produced over a predefined time period as provided by the microcontroller 114.

A second alternating current (AC) comparator 210 counts pulses of a second inductor frequency sample, based on signals received from the second oscillator 206 using the antenna patch 108. In general, the second oscillator 206 will produce a signal with a selected frequency through the antenna patch 108. This signal is produced over a predefined time period as provided by the microcontroller 114 (see FIG. 2A).

In some embodiments, the antenna patch 106 is utilized to sense a reference inductance and antenna patch 108 is utilized to sense soil moisture inductance. It will be understood that the first inductor frequency sample is a reference inductance signal. The second inductor frequency sample is indicative of an inductance of water in the soil.

Pulses from the second oscillator 206 are counted by the second alternating current (AC) comparator 210 and are referred to as soil moisture pulses, which are indicative of an inductance of the soil.

This soil moisture inductance can be compared with the reference inductance to determine a water content measurement for the soil. In some embodiments, additional processing is performed to further refine the water content measurement to account for temperature effects on the oscillators and so forth.

The outputs of both the first alternating current (AC) comparator 208 and the second alternating current (AC) comparator 210 are provided to the microcontroller 114.

Figure 4:
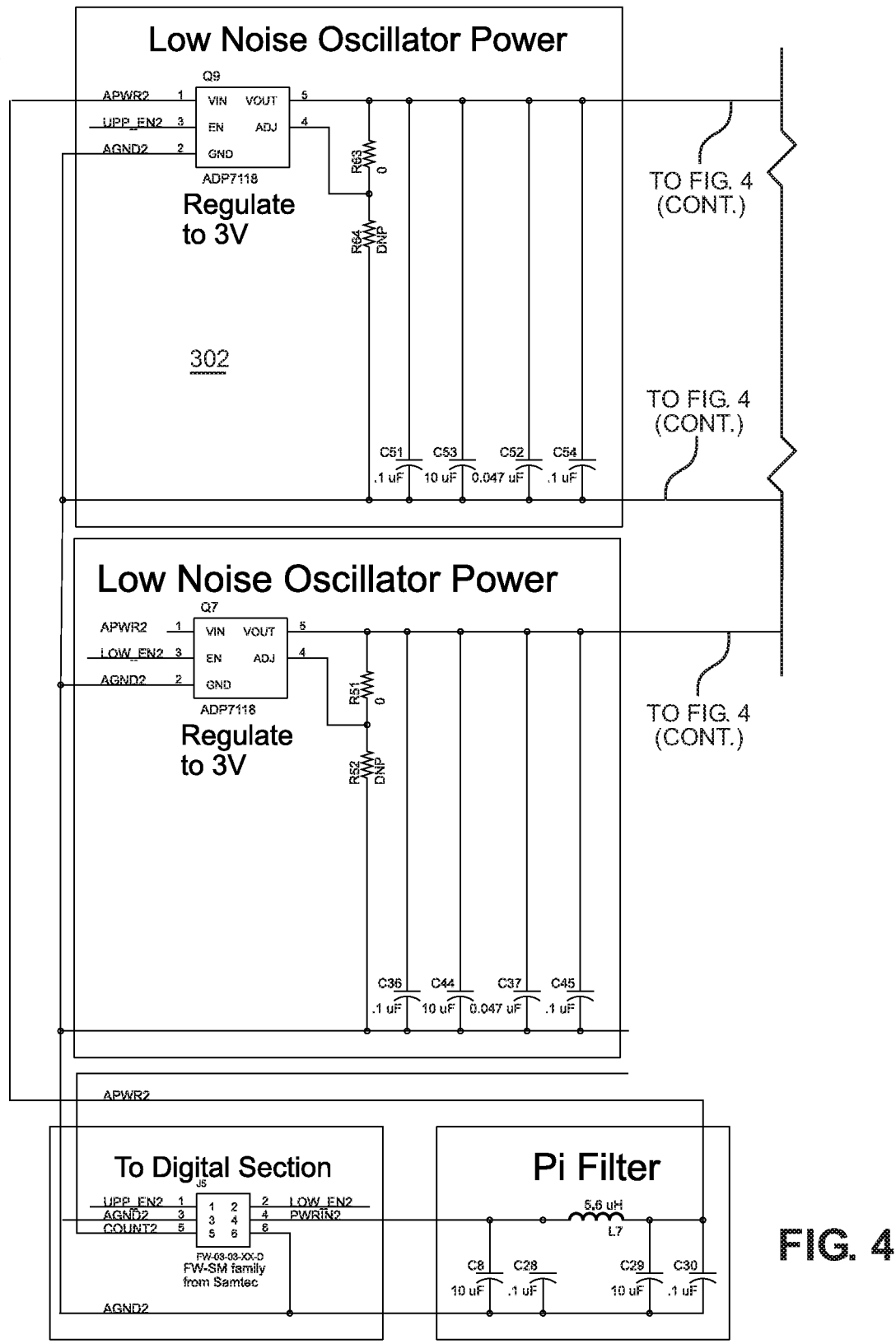
FIG. 4 is a schematic diagram of an example tetrode MOSFET of the soil moisture sensor circuit of FIG. 2A.
Figure 4:
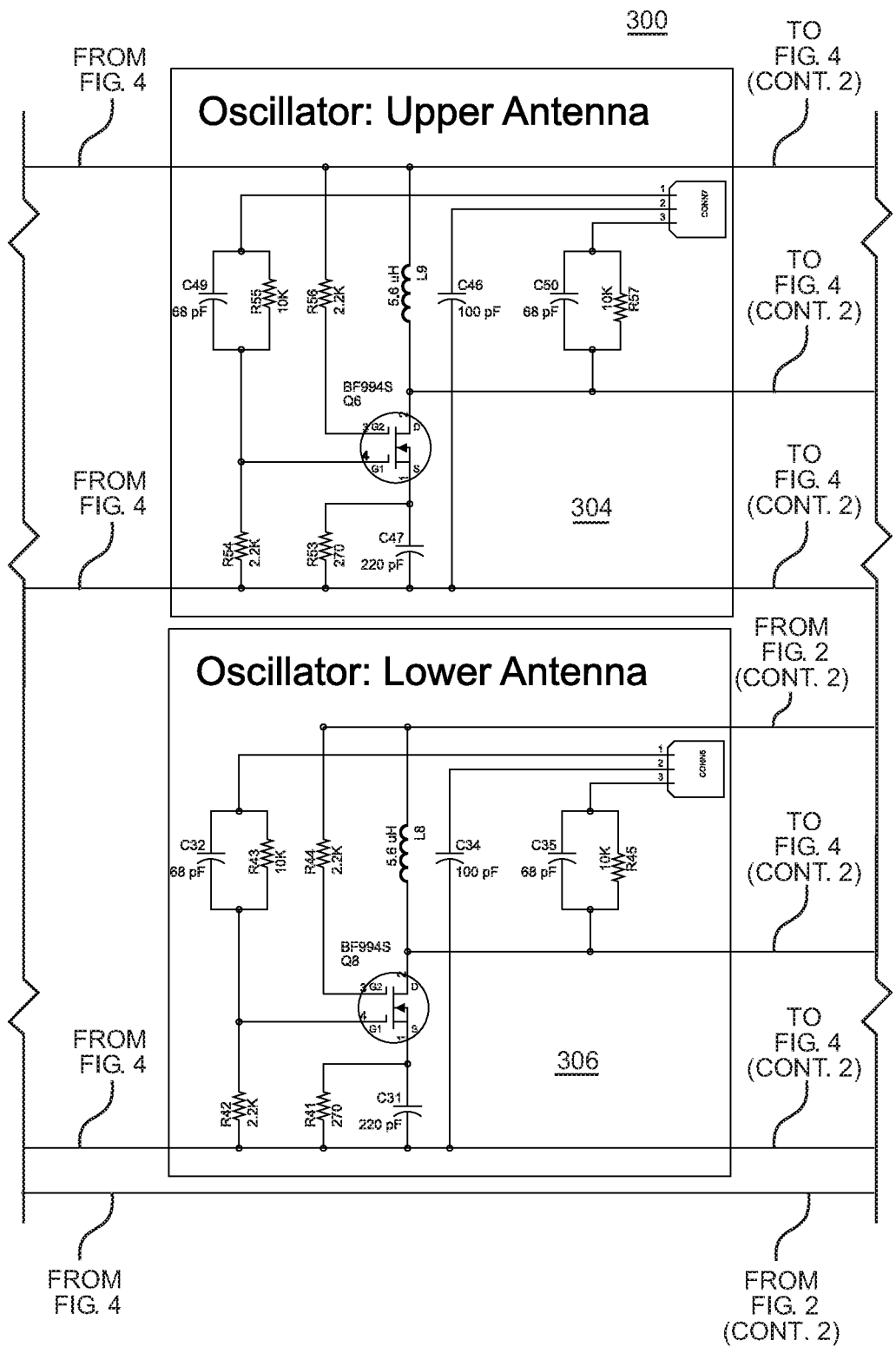
Figure 4:
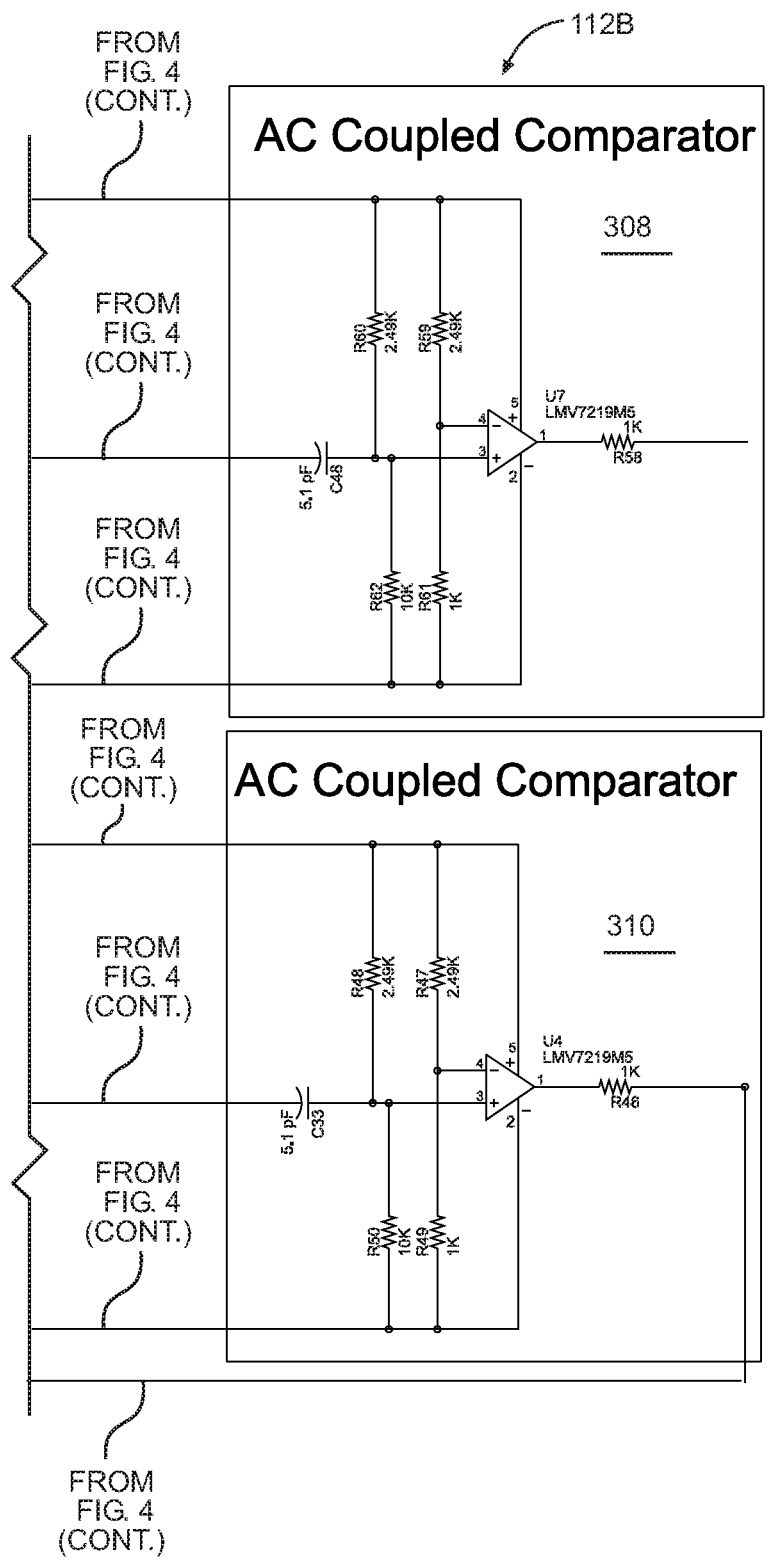

FIGS. 1, 2, and 4 collectively illustrate the transistor circuit 112B in the form of a transistor tetrode or MOSFET tetrode circuit 300. The circuit 300 comprises a low noise oscillator power supply 302, a first oscillator 304 coupled with an upper antenna, such as antenna patch 106 (see FIGS. 1 and 2A), and a second oscillator 306, coupled with a lower antenna, such as antenna patch 108. Another low noise oscillator power supply is coupled to the second oscillator 306.

A first alternating current (AC) comparator 308 counts pulses in a first inductor frequency sample, based on signals received from the first oscillator 304 using antenna patch 106. A second alternating current (AC) comparator 310 counts a second inductor frequency to create a second inductor frequency sample, based on signals received from the second oscillator 306 using antenna patch 108. The outputs of both the first alternating current (AC) comparator 308 and the second alternating current (AC) comparator 310 are provided to the microcontroller 114.

Similarly to the BJT disclosed above, the antenna patch 106 is utilized to sense a reference inductance and antenna patch 108 is utilized to sense moisture inductance in the soil.

It will be understood that the first inductor frequency sample is a reference inductance signal. The second inductor frequency sample is indicative of an inductance of water the soil. These two inductances can be compared with one another to determine a water content measurement for the soil. In some embodiments, additional processing is performed to further refine the comparative water content measurement to account for temperature effects on the oscillators and so forth.

Regardless of the transistor circuit used, the first and second comparators will output pulse counts to the microcontroller 114. The microcontroller 114 also obtains a temperature reading from the temperature sensor 120. The microcontroller 114 then transmits the pulse counts and the temperature reading on the transceiver to the receiver 111.

In some embodiments, rather than receiving pulse counts, such as reference pulse counts and soil moisture pulse counts, the microcontroller 114 can receive the first inductor frequency sample and the second inductor frequency sample. Thus, some embodiments may not require comparators. The microcontroller 114 can utilize an internal counter to count pulses in the first inductor frequency sample and pulses in the second inductor frequency sample.

In some embodiments, the sensor circuit 110 comprises both the bi-junction transistor (BJT) circuit 200 and the MOSFET tetrode circuit 300. In various embodiments, the microcontroller 114 selectively uses either the bi-junction transistor (BJT) circuit 200 or the MOSFET tetrode circuit 300. In other embodiments, either the bi-junction transistor (BJT) circuit 200 or the MOSFET tetrode circuit 300 can be removed from the sensor circuit 110 before deployment. This allows the sensor circuit 110 to be manufactured with both configurations of transistor circuits to reduce manufacturing cost.

The following use case description is from the perspective of the sensor circuit 110 using the BJT 200 of FIG. 3 in view of the schematics of the sensor circuit of FIGS. 2A and 2B. The microcontroller 114 can activate the first oscillator 204, which utilizes the antenna patch 106 to obtain a first inductor frequency sample. The first oscillator 204 is powered by the low noise oscillator power supply 202. This sample is processed using the first alternating current (AC) comparator 208. The first alternating current (AC) comparator 208 counts pulses in the sample. These pulses are referred to as the reference inductance or reference pulses. In some instances, these pulses are counted over a specified period of time.

The second oscillator 206 is powered by the low noise oscillator power supply 202. This sample is processed using the second alternating current (AC) comparator 210. The second alternating current (AC) comparator 210 counts pulses in the sample. These pulses are referred to as the soil moisture inductance or soil moisture pulses. In some instances, these pulses are counted over a specified period of time. This period of time can correspond in duration to the period of time when the reference inductance or reference pulses were counted.

In some embodiments, both the first oscillator 204 and the second oscillator 206 emit signals at the same frequency. In some instances, this shared frequency is above approximately 30 megahertz. The microcontroller 114 can select the frequency in some embodiments. Also, a time period for operation of the oscillators can be selected through the microcontroller 114.

The reference pulses and soil moisture pulses can be transmitted in a raw format to a receiver 111 by the microcontroller 114 over a wired or wireless link. In other instances, the comparison between the reference pulses and soil moisture pulses is determined and transmitted to the receiver 111 by the microcontroller 114.

In some embodiments, the microcontroller 114 can utilize stabilization periods for the oscillators. For example, prior to sensing inductance using the antennas, the microcontroller 114 will power the oscillators and wait for a period of time, referred to as a settling period. After the settling period has expired, inductance signals can be obtained. In some embodiments, these settling periods are not utilized.

In one or more embodiments, the microcontroller 114 can operate the oscillators 204 and 206 in a sequential manner, where reference inductance signals are obtained first and then soil moisture inductance signals are received after. In other embodiments, the oscillators are used in parallel.

In some embodiments, the microcontroller 114 is configured to post-process the reference pulses and soil moisture pulses. Again, as noted above, this post-processing can include performing comparative evaluations where a differential between the reference pulses and soil moisture pulses is determined. This differential value is representative of the moisture content in the soil.

The microcontroller 114 is programmed to either: (1) perform algorithmic processing to convert the sensor counter values (e.g., reference and soil moisture pulses) and temperature measurement to a volumetric water content value; and/or (2) transmit the sensor counter values to the receiver 111, where the receiver 111 performs these calculations.

The microcontroller 114 can thus determine a difference in pulse frequency between the two inductors sampled, along with the temperature of the sensor at a point in time when the two inductors sampled. By calibrating the values of the frequencies in both air, and fully saturated water for each sensor—one can calculate the moisture content by linearly interpolating the frequency change based on moisture content. As the oscillators change frequencies due to temperature, a further adjustment is applied, commonly known as temperature compensation.

Figure 5:
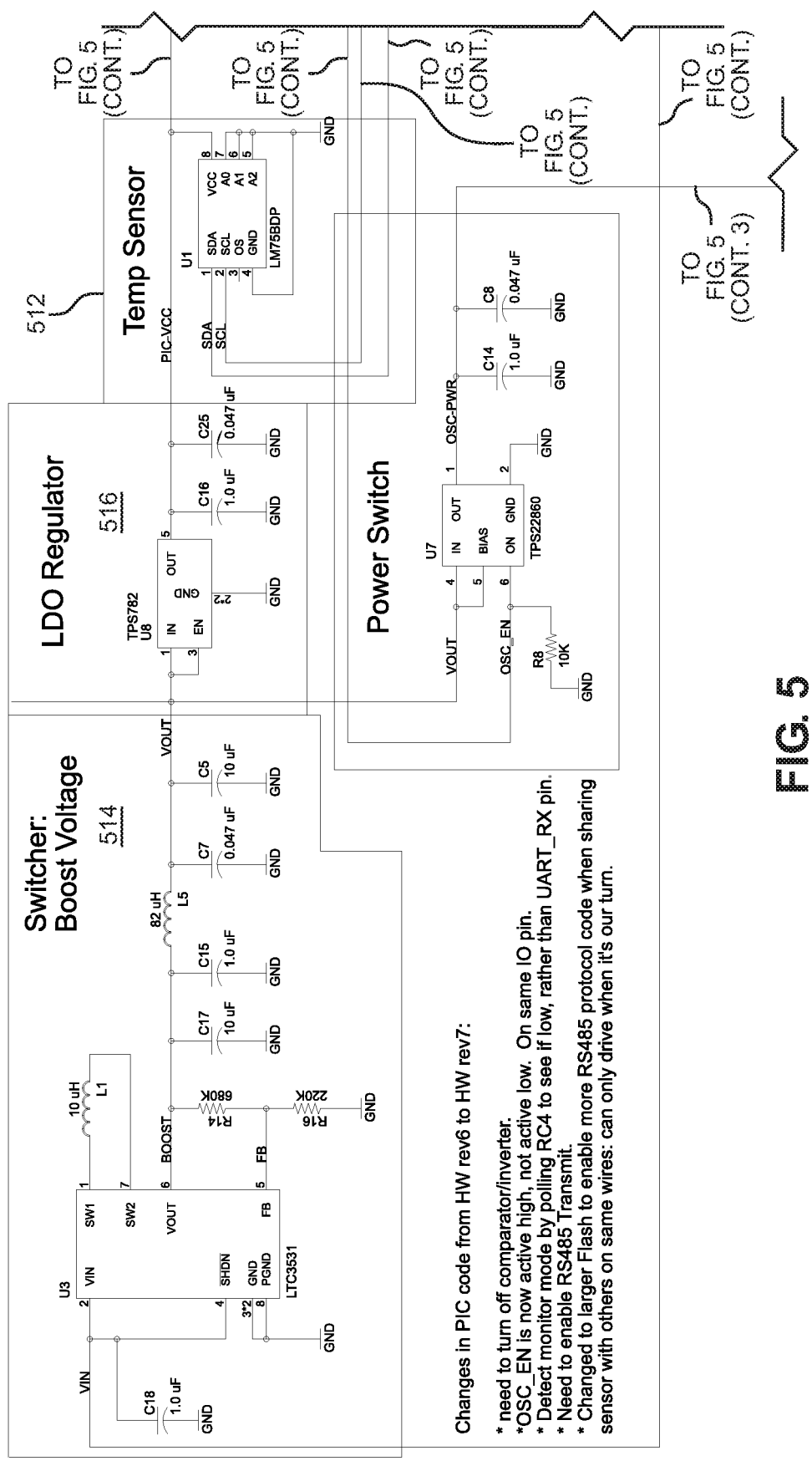
FIG. 5 is a schematic diagram of another example soil moisture sensor circuit used in a soil moisture sensor of the present disclosure.
Figure 5:
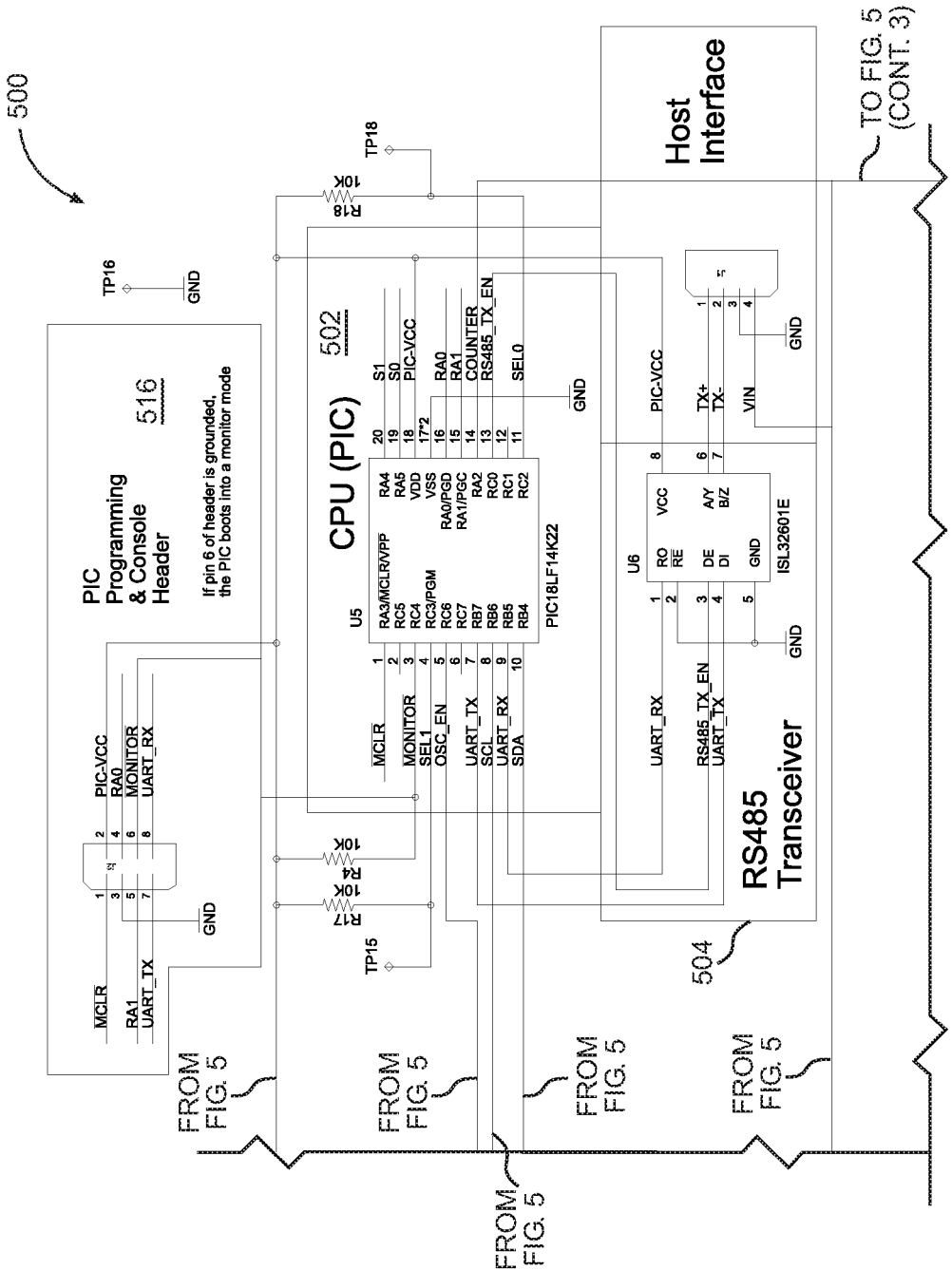

FIG. 5 is a schematic diagram of another example soil moisture sensor circuit (sensor circuit 500) that can be utilized in accordance with the present disclosure. In general, the sensor circuit 500 will utilize a single oscillator or tank circuit for two or more antennas. This configuration is in contrast with the embodiments of FIGS. 1-4 which utilized a separate oscillator for each antenna. In accordance, the sensor circuit 500 comprises a multiplexer that receives signals from the two or more antennas.

In more detail, the sensor circuit 500 comprises a microcontroller 502, a transceiver 504, an oscillator 506, a comparator 508, a multiplexing and switching module 510, and temperature sensor 512. Additional components or modules include a voltage switcher 514, a linear dropout regulator 516, a programming interface 518, and a power switch.

In some embodiments, the transceiver 504 receives signals or message from the microcontroller 502 such as frequency inductance samples, sample counts, soil moisture values (compensated and/or raw values), temperature readings, and so forth. As with other embodiments, these signals or messages can be transmitted to a receiver (not shown) such as a server or base station.

The oscillator 506 can comprise a bi-junction transistor in some instances. The oscillator 506 is configured to generate signals at a particular frequency. These signals are transmitted to two sets of antennas. For example, the oscillator 506 is electrically and communicatively coupled to a first set of internal inductors 520A and 520B and a second set of external or mutual inductors 522A and 522B. The oscillator 506 is coupled to the antennas through a multiplexer 524 of the multiplexing and switching module 510. To be sure, the components designated as antennas/inductors are identified on the diagram of FIG. 5 as line interfaces that connect the antenna patches to multiplexer 524.

In some embodiments, the first set of internal inductors 520A and 520B are utilize to obtain signals that are indicative of a reference inductance and the second set of external or mutual inductors 522A and 522B are used to obtain signals that are indicative of a soil moisture inductance.

The oscillator 506 can transmit a selected frequency to the first set of internal inductors 520A and 520B over a period of time to generate a first inductance sample. The oscillator 506 can transmit a selected frequency to the second set of internal inductors 520A and 520B or external or mutual inductors 522A and 522B over a period of time to generate a second inductance sample. These samples are received and then multiplexed at the multiplexer 524 and then transmitted to the comparator 508.

As with the embodiments of FIGS. 1-4, the comparator 508 is used to count pulses in the samples received from the multiplexer 524. These pulse counts are indicative of reference inductance and soil moisture inductance.

After the pulse counts are obtained by the comparator 508, the pulse counts are transmitted by the comparator 508 to the microcontroller 502. As with the embodiments of FIGS. 1-4, the microcontroller 502 can perform various soil moisture calculations on the pulse counts in order to obtain a soil moisture content value. This can include compensating for the reference inductance, as well as temperature variations. Thus, in some embodiments, the microcontroller 502 can obtain temperature readings from the temperature sensor 512 over the period of time when samples were obtained.

Figure 6:
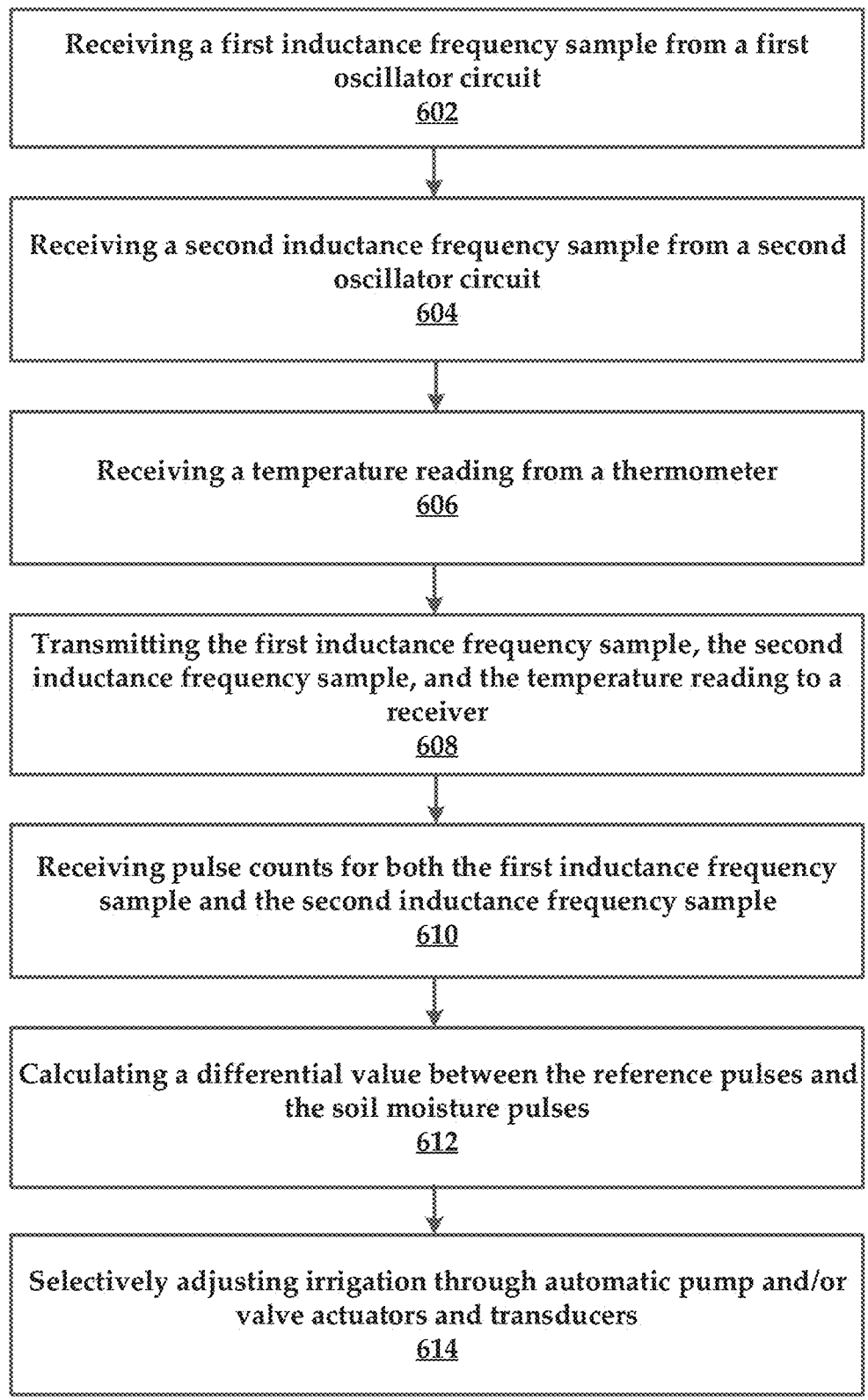
FIG. 6 is a flowchart of an example method of sensing soil moisture content in an area of soil using one or more of the soil moisture sensing devices of the present disclosure.

FIG. 6 is a flowchart of an example method of the present disclosure. The method of FIG. 6 will be understood to be executed by the microcontroller of a sensor of the present disclosure. Specifically, the method of FIG. 6 is performed within the context of the sensor circuit, such as the sensor circuit of the embodiments of FIGS. 1-4.

In some embodiments, the method includes a step 602 of receiving a first inductance frequency sample from a first oscillator circuit. As noted above, the first oscillator circuit is coupled with one or more reference inductors that sense a reference inductance. These reference inductors can include patch antennas or other similar antennas.

In various embodiments, the method includes a step 604 of receiving a second inductance frequency sample from a second oscillator circuit. Again, the second oscillator circuit is coupled with one or more mutual inductors that sense soil moisture inductance in an area of soil.

In one or more embodiments, the method includes a step 606 receiving a temperature reading from a thermometer. The temperature reading is obtained by a microcontroller during periods of time when the first inductance frequency sample and the second inductance frequency sample were obtained. These time periods can include the same time period when the first and second samples are obtained at the same time. In other instances the periods of time are distinct, such as when the first inductance frequency sample and the second inductance frequency sample are obtained at different times.

In some embodiments, the method includes a step 608 of transmitting the first inductance frequency sample, the second inductance frequency sample, and the temperature reading to a receiver. Soil moisture content can be determined by the receiver by applying one or more algorithms as disclosed herein.

In other embodiments, the microcontroller is configured to determine soil moisture content. For example, the method can include an optional step 610 of receiving pulse counts for both the first inductance frequency sample and the second inductance frequency sample. These pulse counts can be determined by a counter in the microcontroller or by way of one or more compensators that count pulses. As noted herein, the pulse count of the first inductance frequency sample is referred to as a reference pulse count. The pulse count of the second inductance frequency sample is referred to as a soil moisture pulse count.

calculating a differential value between the reference pulses and the soil moisture pulses, the differential being indicative of the soil moisture inductance Next, the method includes a step 612 of calculating a differential value between the reference pulses and the soil moisture pulses. The differential is indicative of the soil moisture inductance.

In some embodiments, the method can include processing the soil moisture inductance using techniques such as linear interpolation and temperature compensation in order to refine the soil moisture inductance.

In various embodiments, the method includes a step 614 of selectively adjusting irrigation through automatic pump and/or valve actuators and transducers. For example, when a soil moisture inductance is calculated that indicates that the area of soil has a moisture content that is below an expected moisture threshold, the microcontroller can be configured to transmit a signal that selectively adjusts pumps and/or valves of an irrigation system to increase and/or decrease the flow of water to an area of soil.

Thus, the microcontroller can be configured to use moisture thresholds. In other embodiments, the receiver utilizes moisture thresholds and performs moisture content comparisons to these thresholds.

Thus, the microcontroller can selectively adjust operation of an irrigation system through direct or indirect control of automatic pump and/or valve actuators and transducers.

As noted throughout, steps 610-614 can be alternatively performed by a receiver system, such as a server in an irrigation control system.

According to some embodiments, another example soil moisture sensor can comprise a microcontroller, a single oscillator, and a single antenna. This device can be positioned inside a housing, such as the tubular housings described above. Prior deploying the sensor in an area of soil, a calibration factor for the sensor can be determined by operating the sensor in a dry environment and secondly operating the sensor in a wet environment. For example, a first inductance sample can be obtained when the sensor is in a dry environment. Pluses are counted from the first inductance sample. The device can then be submerged in water and a second inductance sample obtained. Pluses are counted from the second inductance sample. Next, a calibration factor is determined by comparison of these two pulse counts in these controlled environments. The calibration factor is a differential value between the dry sample and the wet sample in some instances. When the calibration factor is obtained, it can be stored on the microcontroller or on a server. To be sure, this calibration factor is unique to each individual sensor and can be determined by a manufacturer or an end user prior to deployment in soil.

After the soil moisture sensor is deployed into an area of soil, a frequency inductance sample is obtained using the single oscillator and antenna. When a pulse count is determined from the frequency inductance sample, the pulse count is modified by application of the calibration factor to obtain a soil moisture content value. Additional compensation for temperature changes can also be utilized to fine tune the soil moisture content value.

Some embodiments of the present disclosure can utilize a plurality of antennas as noted above. In some embodiments, these antennas can be positioned around tubular substrate. Also, sensor units (comprised of at least one antenna and one sensor circuit) can be arranged around the tubular substrate at radial offsets relative to one another. Each sensor unit can broadcast signal frequency into a discrete sector. For example, if four sensor units are deployed on the tubular substrate, each sensor unit can be clocked in its position in order to broadcast in a 90 degree radial area. Each sensor unit will broadcast in its own a 90 degree radial area with minimal overlap at the edges. In some embodiments, the sensor units can be separated by a dielectric to isolate their broadcast areas from that of other sensor units.

In one or more embodiments, the sensor circuit of a device of the present disclosure can be configured to obtain frequency samples at a plurality of frequencies. This can be advantageous in determining not only moisture content, but also constituent particulate content present in the soil moisture. For example, if water used to irrigate an area of soil becomes contaminated with salt, the sensing of the soil moisture at different frequencies can be used to determine a salinity of the water in the soil. By way of example, assume that salt moves at a frequency of 10 megahertz, but salt does not move at 30 megahertz, but water molecules will. When inductance is measured at both 10 megahertz and 30 megahertz, these values can be used to calculate an approximate salinity or salt content in the water in the soil.

Thus, the technology described herein can be utilized not only to sensing moisture content in soil, but also for measuring particulate levels in a fluid. For example, knowing inductance frequencies for salt, potassium, magnesium, lead, and other common water particulates, a sensor of the present disclosure can be tuned to different frequencies in order to obtain inductance samples at each frequency. Based on pulses counted for each of the samples, it is possible to quantify a volumetric value of each of these particulates in a water sample.

In yet other embodiments, sensor circuits of the present disclosure can be configured to vary voltage applied during inductance sampling in order to sense moisture content in soil at given distances from a sensor circuit or device. Using the devices disclosed herein, using lower to higher voltage when obtaining inductance samples, the sensor circuit(s) can obtain soil moisture content values out to specific distances from the sensor circuits. For example, at a lowest voltage, the soil moisture content values are obtained outward from the sensor circuit to a diameter of four feet. When measured at a slightly higher voltage, the soil moisture content values are obtained outward from the sensor circuit to a second diameter of seven feet. When measured at a highest voltage, the soil moisture content values are obtained outward from the sensor circuit to a third diameter of twelve feet. To be sure, these are merely example distances. The exact voltages and distances measured are a matter of sensor design and operational constraints.

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the present technology in the form disclosed. Many modifications and variations will be apparent to those of ordinary skill in the art without departing from the scope and spirit of the present technology. Exemplary embodiments were chosen and described in order to best explain the principles of the present technology and its practical application, and to enable others of ordinary skill in the art to understand the present technology for various embodiments with various modifications as are suited to the particular use contemplated.

Aspects of the present technology are described above with reference to flowchart illustrations and/or block diagrams of methods, apparatus (systems) and computer program products according to embodiments of the present technology. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

In the following description, for purposes of explanation and not limitation, specific details are set forth, such as particular embodiments, procedures, techniques, etc. in order to provide a thorough understanding of the present invention. However, it will be apparent to one skilled in the art that the present invention may be practiced in other embodiments that depart from these specific details.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

Also, some embodiments may be described in terms of "means for" performing a task or set of tasks. It will be understood that a "means for" may be expressed herein in terms of a structure, such as a processor, a memory, an I/O device such as a camera, or combinations thereof. Alternatively, the "means for" may include an algorithm that is descriptive of a function or method step, while in yet other embodiments the "means for" is expressed in terms of a mathematical formula, prose, or as a flow chart or signal diagram.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It is noted at the outset that the terms "coupled," "connected", "connecting," "electrically connected," etc., are used interchangeably herein to generally refer to the condition of being electrically/electronically connected. Similarly, a first entity is considered to be in "communication" with a second entity (or entities) when the first entity electrically sends and/or receives (whether through wireline or wireless means) information signals (whether containing data information or non-data/control information) to the second entity regardless of the type (analog or digital) of those signals. It is further noted that various figures (including component diagrams) shown and discussed herein are for illustrative purpose only, and are not drawn to scale.

If any disclosures are incorporated herein by reference and such incorporated disclosures conflict in part and/or in whole with the present disclosure, then to the extent of conflict, and/or broader disclosure, and/or broader definition of terms, the present disclosure controls. If such incorporated disclosures conflict in part and/or in whole with one another, then to the extent of conflict, the later-dated disclosure controls.

The terminology used herein can imply direct or indirect, full or partial, temporary or permanent, immediate or delayed, synchronous or asynchronous, action or inaction. For example, when an element is referred to as being "on," "connected" or "coupled" to another element, then the element can be directly on, connected or coupled to the other element and/or intervening elements may be present, including indirect and/or direct variants. In contrast, when an element is referred to as being "directly connected" or "directly coupled" to another element, there are no intervening elements present.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be necessarily limiting of the disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence or addition of one or more other features, integers, steps, operations, elements, components, and/or groups thereof.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing and/or other any other types of manufacturing. For example, some manufacturing processes include three dimensional (3D) printing, laser cutting, computer numerical control (CNC) routing, milling, pressing, stamping, vacuum forming, hydroforming, injection molding, lithography and/or others.

Any and/or all elements, as disclosed herein, can include, whether partially and/or fully, a solid, including a metal, a mineral, a ceramic, an amorphous solid, such as glass, a glass ceramic, an organic solid, such as wood and/or a polymer, such as rubber, a composite material, a semiconductor, a nano-material, a biomaterial and/or any combinations thereof. Any and/or all elements, as disclosed herein, can include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, non-transparency, luminescence, anti-reflection and/or holographic, a photo-sensitive coating, an electronic and/or thermal property coating, such as for passivity, insulation, resistance or conduction, a magnetic coating, a water-resistant and/or waterproof coating, a scent coating and/or any combinations thereof.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

Furthermore, relative terms such as "below," "lower," "above," and "upper" may be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings is turned over, then the elements described as being on the "lower" side of other elements would then be oriented on "upper" sides of the other elements. Similarly, if the device in one of the figures is turned over, elements described as "below" or "beneath" other elements would then be oriented "above" the other elements. Therefore, the example terms "below" and "lower" can, therefore, encompass both an orientation of above and below.

While various embodiments have been described above, it should be understood that they have been presented by way of example only, and not limitation. The descriptions are not intended to limit the scope of the invention to the particular forms set forth herein. To the contrary, the present descriptions are intended to cover such alternatives, modifications, and equivalents as may be included within the spirit and scope of the invention as defined by the appended claims and otherwise appreciated by one of ordinary skill in the art. Thus, the breadth and scope of a preferred embodiment should not be limited by any of the above-described exemplary embodiments.

What is claimed is:

1. A soil moisture monitor device, the device comprising:
a first oscillator circuit coupled with one or more reference inductors to emit a first inductance frequency;
a second oscillator circuit coupled with one or more mutual inductors to emit a first inductance frequency into an area of soil;
a microcontroller electrically coupled to the first oscillator circuit and the second oscillator circuit;
a housing positioned within the area of soil, the housing comprising an inner tubular substrate that receives the one or more reference inductors, the one or more mutual inductors, the first oscillator circuit, the second oscillator circuit, and the microcontroller, the microcontroller being configured to:
obtain a first inductance frequency sample using the one or more reference inductors;
obtain a second inductance frequency sample using the one or more mutual inductors;
obtain a temperature reading from a thermometer; and
transmit the first inductance frequency sample, the second inductance frequency sample, and the temperature reading to a receiver; and
a first compensator that counts reference pulses in the first inductance frequency sample and a second compensator that counts soil moisture pulses in the second inductance frequency sample.

2. The device according to claim 1, wherein the microcontroller is configured to wait for a first oscillator settling period before the first inductance frequency sample is obtained.

3. The device according to claim 2, wherein the microcontroller is configured to turn off power to the first oscillator circuit after the first inductance frequency sample is obtained.

4. The device according to claim 3, wherein the microcontroller is configured to power the second oscillator circuit and wait for a second oscillator settling period before the second inductance frequency sample is obtained.

5. The device according to claim 4, wherein the microcontroller is configured to calculate a differential value between the first inductance frequency sample and the second inductance frequency sample.

6. The device according to claim 5, wherein the microcontroller is configured to utilize the temperature reading to compensate for temperature effects on the first oscillator circuit and the second oscillator circuit.

7. The device according to claim 6, wherein the microcontroller is configured to linearly interpolate the differential value based on calculated moisture content.

8. The device according to claim 1, further comprising an amplifier that receives signals from any of the first oscillator circuit and the second oscillator circuit.

9. The device according to claim 1, further comprising a multiplexer that receives the first inductance frequency sample and the second inductance frequency sample.

10. The device according to claim 9, further comprising at least one other soil moisture monitor device communicatively coupled to the multiplexer.

11. The device according to claim 1, wherein any of the first oscillator circuit and the second oscillator circuit are a transistor selected from a group comprising a bi-junction transistor and a tetrode metal-oxide-semiconductor field-effect transistor.

12. A method, comprising:
receiving a first inductance frequency sample from a first oscillator circuit, the first oscillator circuit being coupled with one or more reference inductors that sense a reference inductance;
receiving a second inductance frequency sample from a second oscillator circuit, the second oscillator circuit being coupled with one or more mutual inductors that sense soil moisture inductance in an area of soil;

selecting a sampling time period for obtaining the first inductance frequency sample and the second inductance frequency sample;

receiving a temperature reading from a thermometer, the temperature reading being obtained when the first inductance frequency sample and the second inductance frequency sample were obtained; and transmitting the first inductance frequency sample, the second inductance frequency sample, and the temperature reading to a receiver.

13. The method according to claim 12, further comprising selecting a frequency for the first oscillator circuit and the second oscillator circuit.

14. The method according to claim 13, wherein the frequency is above 30 megahertz.

15. The method according to claim 12, further comprising:
counting reference pulses of the first inductance frequency sample;
counting soil moisture pulses of the second inductance frequency sample; and
calculating a differential value between the reference pulses and the soil moisture pulses, the differential value being indicative of the soil moisture inductance.

16. The method according to claim 15, further comprising applying a temperature reading to compensate for temperature effects on the first oscillator circuit and the second oscillator circuit so as to refine the soil moisture inductance.

17. The method according to claim 16, further comprising linearly interpolating the differential value based on calculated moisture content.

18. The method according to claim 17, further comprising selectively adjusting operation of an irrigation system so as to increase or decrease water applied to an area of soil based on the calculated moisture content.

19. A soil moisture monitor device, the device comprising:
a first oscillator circuit coupled with one or more reference inductors to emit a first inductance frequency;
a second oscillator circuit coupled with one or more mutual inductors to emit a first inductance frequency into an area of soil;
a microcontroller electrically coupled to the first oscillator circuit and the second oscillator circuit;
a housing positioned within the area of soil, the housing comprising an inner tubular substrate that receives the one or more reference inductors, the one or more mutual inductors, the first oscillator circuit, the second oscillator circuit, and the microcontroller, the microcontroller being configured to:
obtain a first inductance frequency sample using the one or more reference inductors;
obtain a second inductance frequency sample using the one or more mutual inductors;
obtain a temperature reading from a thermometer; and
transmit the first inductance frequency sample, the second inductance frequency sample, and the temperature reading to a receiver; and
a multiplexer that receives the first inductance frequency sample and the second inductance frequency sample.

* * * * *